United States Patent [19] [11] 4,217,292
Kroenke [45] Aug. 12, 1980

[54] PROCESS FOR MAKING AMINE MOLYBDATES

[75] Inventor: William J. Kroenke, Brecksville, Ohio

[73] Assignee: The B. F. Goodrich Company, Akron, Ohio

[21] Appl. No.: 16,583

[22] Filed: Mar. 1, 1979

[51] Int. Cl.$^2$ .............................................. C07F 11/00
[52] U.S. Cl. .................................. 260/429 R; 544/4; 544/64; 544/181; 546/8
[58] Field of Search ..................... 260/429 R; 544/181, 544/4, 64; 546/8

[56] References Cited

U.S. PATENT DOCUMENTS

| | | | |
|---|---|---|---|
| 2,909,541 | 10/1959 | Huzel | 260/429 R |
| 2,938,869 | 5/1969 | Huzel | 260/429 R X |
| 3,223,625 | 12/1965 | Cyphers et al. | 260/429 R X |
| 3,282,838 | 11/1966 | Knowles et al. | 260/429 R X |
| 3,290,245 | 12/1966 | Elliott et al. | 260/429 R X |
| 3,349,108 | 10/1967 | Marzluff | 260/429 R |
| 3,489,775 | 1/1970 | de Roch et al. | 260/429 R X |
| 4,009,122 | 2/1977 | Lines et al. | 260/429 R |
| 4,053,455 | 10/1977 | Kroenke | 260/45.75 R |

*Primary Examiner*—Helen M. S. Sneed
*Attorney, Agent, or Firm*—James R. Lindsay

[57] ABSTRACT

Amine molybdates are formed by reacting molybdenum trioxide ($MoO_3$) with an amine in an aqueous medium essentially free of acid and in which is dissolved a water-soluble ammonium or monovalent metal or divalent metal or trivalent rare earth metal salt of an acid, or a combination thereof. Although the reaction may be carried out at room temperature, the reaction mixture desirably is heated to between about 75° C. to 110° C. and preferably is refluxed to reduce the time required for completion of the reaction. The reaction slurry is stirred while the reaction is occurring. Upon completion of the reaction, the amine molybdate is separated from the liquid phase, and is washed and dried. After removal of the solid amine molybdate from the slurry the liquid component can be reused avoiding possible environmental difficulties.

12 Claims, No Drawings

PROCESS FOR MAKING AMINE MOLYBDATES

BACKGROUND OF THE INVENTION

Although vinyl chloride and vinylidene chloride polymers are known to be self-extinguishing and relatively more flame retardant than polymers such as polyethylene and polypropylene, a substantial amount of smoke generally is produced upon the exposure of vinyl chloride or vinylidene chloride polymers to fire. As a consequence, various smoke retardant materials have been added to vinyl chloride polymers and vinylidene chloride polymers to reduce the quantity of smoke produced in the event the polymer is exposed to a flame.

U.S. Pat. No. 4,053,455 teaches the use of amine molybdates as effective smoke retardant additives for vinyl chloride and vinylidene chloride polymers, and suggests the use of melamine molybdate as being preferred since it is white in color, highly effective as a smoke retardant and processes easily without discoloring the polymers. The amine molybdates may be used as the sole smoke retardant, but in some instances are advantageously used in combination with other known smoke retardants. U.S. Pat. No. 4,053,451 describes the use of mixtures of melamine molybdate or substituted melamine molybdates and certain copper compounds as smoke retardants for vinyl chloride polymers and vinylidene chloride polymers. U.S. Pat. No. 4,053,453 discloses the use of copper oxalate with amine molybdates as a smoke retardant mixture.

Amine molybdates may be produced by reacting an amine with a molybdenum compound such as molybdenum trioxide ($MoO_3$), molybdic acid or a molybdenum salt in an acidic aqueous medium made acidic through the addition of a suitable acid such as an organic acid containing 1 to 12 carbon atoms (exemplified by acetic acid, propionic acid, benzoic acid, and the like) or an inorganic acid (exemplified by hydrochloric acid, nitric acid or sulfuric acid). Excellent results have been obtained using ammonium dimolybdate, ammonium heptamolybdate, sodium molybdate, or commercial "molybdic acid" (which primarily consists of one or more ammonium molybdates) as the molybdenum compound. The preferred reaction method comprises adding an aqueous solution of ammonium molybdate or other molybdenum salt to an acidic solution of the amine. The acidic mixture is refluxed until the reaction is complete, usually for about ¼ to 4 hours. Alternatively, all of the components of the mixture are charged essentially simultaneously to the reaction vessel followed by refluxing of the mixture until the reaction is completed. The mixture preferably is stirred continuously during the period that reaction is occurring.

SUMMARY OF THE INVENTION

The process of the present invention for making amine molybdates comprises reacting essentially stoichiometric quantities of molybdenum trioxide with an amine in an aqueous medium in the presence of a water-soluble ammonium or monovalent metal or divalent metal or trivalent rare earth metal salt of an inorganic or organic acid, or a combination of one or more of them. If the amine is not readily soluble in water, an alcohol added to the aqueous mixture can produce a favorable effect. An oxidizing agent desirably is present in the reaction mixture to insure that the molybdenum atoms in the molybdate formed remains in its highest state of oxidation (i.e., $Mo^{6+}$). Although the reaction between the amine and molybdenum trioxide can occur at room temperature, desirably the reaction mixture is heated to between about 75° to 110° C., preferably to 90° to 110° C., and preferably is refluxed to reduce the time required for the reaction to be completed. The reaction mixture preferably is stirred continuously while the reaction is occurring. Although the time required for completion of the reaction will vary depending in part upon the temperature at which it is carried out, usually the mixture is reacted for from ¼ to 4 hours. In many reactions, the yield will approach 100% of the theoretical yield.

Upon completion of the reaction, the solid amine molybdate formed is separated from the liquid phase by filtration, centrifugation or other suitably separation means, and is washed and dried. The reacted mixture may be cooled to room temperature (about 25° C.) before the separation of the solid amine molybdate from the liquid, if desired, although cooling the mixture before the separation of the solid material from the liquid phase is not necessary. The recovered amine molybdate may be air dried, preferably at about 100° to 200° C., or may be vacuum dried, preferably at temperatures up to 150° C. and higher. The amine molybdate is readily identifiable by elemental, infrared or x-ray diffraction analysis.

The reaction of the present invention is exemplified by the following equation:

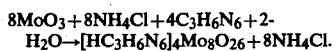

$$8MoO_3 + 8NH_4Cl + 4C_3H_6N_6 + 2H_2O \rightarrow [HC_3H_6N_6]_4Mo_8O_{26} + 8NH_4Cl.$$

As is evident from the above equation, the same amount of ammonium chloride is present as dissolved salt in the liquid phase after the reaction is completed as was present in the original reaction mixture. After separation of the amine molybdate from the liquid phase following completion of the reaction, the remaining liquid phase can be reused in its entirety avoiding possible environmental difficulties. The small quantity of water involved in the reaction and the water remaining in the "filter cake" can be replenished from time-to-time to maintain the consistency of the reaction mixture essentially the same from batch to batch. Also, small additions of the water-soluble salt may be made from time-to-time (to replace salt that is retained in the "filter cake") to keep the concentration level of the water-soluble salt in the reaction mixture essentially constant.

The presence of the water-soluble salt in the reaction mixture reduces the presence of impurity phases in the amine molybdate product, reduces the reaction time within which to achieve a complete reaction, and helps to avoid discoloration in the recovered solid product caused by unreacted $MoO_3$ or as a consequence of the reduction of the valence of the molybdenum in the amine molybdate formed from $Mo^{+6}$ to $Mo^{+5}$.

DETAILED DESCRIPTION OF THE INVENTION

Amine molybdates are produced in accordance with this invention by reacting essentially stoichiometric quantities of molybdenum trioxide with an amine in an aqueous medium essentially free of acid and in which a water-soluble ammonium or monovalent metal or divalent metal or trivalent rare earth salt of an inorganic or organic acid is dissolved.

Amines suitable for preparing the amine molybdates using the process of this invention include polymeric amines, as well as simple amines. The simple amines may contain from 1 to 75 carbon atoms and from 1 to 10 primary, secondary, or tertiary amine groups or a mixture thereof, more preferably from 1 to 6 groups. Simple amines include aliphatic, alicyclic, aromatic and heterocyclic amines. Examples of suitably polymeric amines include polyethyleneimine, polyvinylpyridine, polyvinylpyrrolidine and poly(2,24-trimethyl-1,2-dihydroquinolyl). Examples of suitable simple amines include aliphatic amines such as ethylamine, ethylenediamine, 1,2-propanediamine, 1,3-propanediamine, 1,4-butanediamine, 2-methyl-1,2-propanediamine, 1,5-pentanediamine, 1,6-hexanediamine, 1,7-heptanediamine, 1,8-octanediamine, 1,10-decanediamine, 1,12-dodecanediamine, and the like. Also suitable are aliphatic amines such as diethylenetriamine, triethylenetetramine, tetraethylene-pentamine, bis(hexamethylene)triamine, 3,3'-iminobispropylamine, guanidine carbonate, and the like. Other suitable amines include alicyclic diamines and polyamines such as 1,2-diaminocyclohexane, 1,8-p-menthanediamine, and the like, aromatic amines such as aniline, N,N-dimethylaniline, and the like, and heterocyclic amines such as melamine and substituted melamines, ammeline, pyridene, piperazine, hexamethylenetetramine, 2,2,4-trimethyl decahydroquinoline, and N-(aminoalkyl)-piperazines wherein each alkyl group contains from 1 to 12 carbon atoms, more preferably 1 to 6 carbon atoms, such as N-(2-aminoethyl)-piperazine and the like. Melamine is preferred since a melamine molybdate can be produced that is white in color, highly effective as a smoke retardant and processes easily without discoloring polymers (such as polyvinyl chloride and polyvinylidene chloride) to which it is added.

Sufficient water is included in the reaction mixture to insure a reaction medium that has a consistency that enables it to be easily stirred.

The water-soluble salt dissolved in the aqueous medium of the reaction mixture may be an ammonium or monovalent metal or divalent metal or trivalent rare earth metal salt of a strong acid (HCl, $HNO_3$ and $H_2SO_4$) or of a weak acid (such as carbonic acid, acetic acid, formic acid, benzoic acid, salicyclic acid, oxalic acid, sebacic acid and adipic acid), or a combination of one or more of the salts. Excellent results are obtained using the sodium, potassium or ammonium salts of hydrochloric acid, nitric acid and sulfuric acid and, in particular, ammonium chloride, ammonium sulfate, ammonium bisulfate, ammonium nitrate, sodium sulfate, sodium bisulfate, sodium chloride, potassium sulfate and potassium bisulfate, or combinations of these salts. The water-soluble salt desirably is present in the reaction mixture in an amount to form at least a 1:1 mole ratio with the molybdenum trioxide, but preferably is present in an amount in excess of that necessary to form a 1:1 mole ratio with the molybdenum trioxide to insure a facile reaction which produces a high yield of amine molybdate product of good quality and color.

An oxidizing agent also desirably is included in the reaction mixture to provide additional assurance that the molybdenum atoms in the amine molybdate retain their highest state of oxidation (i.e., $Mo^{6+}$). Suitable oxidizing agents include sodium hypochlorite, hydrogen peroxide, ammonium persulfate, potassium permanganate, potassium periodate, potassium perchlorate, potassium percarbonate, potassium peroxide, sodium percarbonate, sodium periodate, sodium permanganate, sodium peroxide and sodium dichromate. The amount by weight of oxidizing agent used, if any, generally would not exceed about 10 percent of the weight of molybdenum trioxide present in the reaction mixture.

The reaction time for obtaining the highest yield of amine molybdate will vary depending in part upon the temperature at which the reaction is occurring and the amount of excess alkaline salt present in the reaction mixture. However, the reaction usually is completed within four hours and, when the water-soluble salt is present in about a 50 percent excess, may be completed in ¼ to 2 hours or even less.

Following completion of the reaction, the solid amine molybdate is removed from the liquid phase by filtration or centrifugation or by another separation technique. The mixture can be cooled to about room temperature (25° C.) before separating the amine molybdate from the liquid phase, but cooling is not necessary.

The amine molybdate separated from the liquid phase is washed with water and/or alcohol and then is dried. Drying can be carried out in an air oven, desirably at a temperature of about 100°–200° C., or by vacuum drying, preferably at temperatures up to 150° C. or higher.

The following examples illustrate the invention more fully:

EXAMPLE 1

Melaminium heptamolybdate was prepared as follows, 10.00 grams of melamine, 11.41 grams of molybdenum trioxide, 7.86 grams of ammonium sulfate and 300 milliliters of water were added to a 500 milliliter round-bottom flask equipped with a water-cooled condenser.

The reaction mixture was heated to about 100° C. and refluxed for 2 hours while being stirred continuously. Thereafter, the solids were filtered from the liquid phase without cooling. A white solid product was recovered. The product was washed with water and vacuum dried for 2 hours at 100° C. 20.73 grams of the white product (identified by infrared analysis to be melaminium heptamolybdate) was recovered, representing a yield of 93.29 percent of the theoretical yield.

EXAMPLE 2

Dicyclohexylamine and molybdenum trioxide were reacted together in the following manner to form a dicyclohexylamine molybdate with a 2/1 molybdenum/dicyclohexylamine molar ratio. 10.00 grams of dicyclohexylamine, 15.88 grams of molybdenum trioxide, 10.94 grams of ammonium sulfate and 300 milliliters of water were charged into a 500 milliliter round-bottom flask equipped with a water-cooled condenser.

The reaction mixture was refluxed for 2 hours while stirring continuously and then was filtered. An off-white crystalline solid remained on the filter paper. The solid was washed with water and then was vacuum dried for 3 hours at 100° C. Infrared and x-ray diffraction spectroscopic analyses identified the recovered solid to be dicyclohexylammonium octamolybdate. 22.55 grams of the crystalline solid was recovered, representing a yield of 85.51 percent of the theoretical yield.

EXAMPLE 3

Dodecylammonium octamolybdate havng a 2/1 molybdenum/dodecylamine molar ratio was prepared in the following manner. 10.00 grams of dodecylamine, 15.53 grams of molybdenum trioxide, 10.70 grams of ammonium sulfate and 300 milliliters of water were charged into a 500 milliliter round-bottom flask equipped with a water-cooled condenser and was refluxed for 2 hours while stirring continuously. The mixture was cooled to room temperature and filtered. A very light gray crystalline solid was recovered. The recovered solid was washed with water and vacuum dried for 4 hours at 100° C. The solid was determined by infrared and x-ray diffraction analyses to be dodecylammonium octamolybdate. 25.27 grams of the light gray crystalline solid was recovered, representing a yield of 97.11 percent of the theoretical yield.

EXAMPLE 4

Tripentylammonium decamolybdate was prepared by refluxing for 2 hours a reaction mixture comprising 10.00 grams of tripentylamine, 12.66 grams of molybdenum trioxide, 8.72 grams of ammonium sulfate and 300 milliliters of water in a 500 milliliter round-bottom flask fitted with a water-cooled condenser, the mixture being stirred continuously. The mixture then was cooled to room temperature and filtered. A light green crystalline solid was recovered and was washed with water and vacuum dried for 5 hours at 100° C. Infrared and x-ray diffraction analyses identified the solid to be tripentylammonium decamolybdate. 17.48 grams of the crystalline solid was recovered, representing a yield of 75.84 percent of the theoretical yield.

EXAMPLE 5

Anilinium decamolybdate having a 2.5/1 molybdenum/aniline molar ratio was prepared in the following manner. 10.00 grams of aniline, 30.91 grams of molybdenum trioxide, 21.29 grams of ammonium sulfate and 300 milliliters of water were added to a 500 milliliter round-bottom flask equipped with a water-cooled condenser. The mixture was refluxed for 2 hours while being stirred continuously, and was cooled to room temperature and filtered. A white crystalline solid was recovered. The recovered solid was washed with water and was vacuum dried for 2½ hours at 100° C. The solid was identified by infrared and x-ray diffraction analyses to be anilinium decamolybdate. 37.15 grams of the white crystalline solid was recovered, representing a yield of 88.71% of the theoretical yield.

EXAMPLE 6

Melaminium octamolybdate having a 2/1 molybdenum/melamine molar ratio was prepared in the following manner. 10 grams of melamine, 22.83 grams of molybdenum trioxide, 15.72 grams of ammonium sulfate and 300 milliliters of water were added to a 500 milliliter round-bottom flask equipped with a water-cooled condenser. The mixture was refluxed at about 105° C. for 2 hours while being stirred continuously and then was cooled to room temperature and filtered. A white crystalline solid was recovered from the liquid phase. The white product was washed with water and vacuum dried for 1½ hours at 120° C. The white product was identified to be melaminium octamolybdate by infrared and x-ray diffraction analyses. 33.15 grams of the white solid product was recovered, representing a yield of 98.84 percent of the theoretical yield.

EXAMPLE 7

Ammonium melaminium octamolybdate was prepared by adding 10.00 grams of melamine, 22.83 grams of molybdenum trioxide, 12.42 grams of ammonium acetate and 300 milliliters of water to a 500 milliliter round-bottom flask equipped with a water-cooled condenser. The mixture was refluxed for 2 hours at about 105° C. with continuous stirring and then was allowed to cool to room temperature and was filtered. A white crystalline solid was recovered. The white product was washed with water and vacuum dried for 2 hours at 100° C. The product was identified by infrared and x-ray diffraction analyses to be ammonium melaminium octamolybdate. 34.16 grams of the white product were recovered, representing a yield of 98.30 percent of the theoretical yield.

EXAMPLE 8

Ammonium melaminium octamolybdate was prepared by adding 10.00 grams of melamine, 22.83 grams of molybdenum trioxide, 15.00 grams of ammonium formate and 300 milliliters of water to a 500 milliliter round-bottom flask provided with a water-cooled condenser. The mixture was refluxed at about 105° C. for 2 hours while being continuously stirred and then was cooled to room temperature and filtered. A white crystalline product was recovered and washed with water and vacuum dried at 100° C. for 2½ hours. The white crystalline product was identified to be ammonium melaminium octamolybdate by infrared and x-ray diffraction analyses. 34.36 grams of the product were recovered, representing a yield of 98.88 percent of the theoretical yield.

The following Examples 9 through 23 illustrate the use of other water-soluble salts in the preparation of melaminium octamolybdate having a 2/1 molybdenum/melamine molar ratio using the process of this invention.

EXAMPLE 9

Melaminium octamolybdate having a 2/1 molybdate/melamine molar ratio was prepared by the following procedure. 10.00 grams of melamine, 22.83 grams of molybdenum trioxide, 39.09 grams of epsom salt ($MgSO_4.7H_2O$) and 300 milliliters of water were added to a 500 milliliter round-bottom flask fitted with a water-cooled condenser. The mixture was refluxed at about 105° C. for 2 hours while being stirred continuously, cooled to room temperature and filtered. A white crystalline product was recovered. The recovered product was washed with water and vacuum dried at 100° C. for 1½ hours. The product was identified by infrared and x-ray diffraction analyses to be melaminium octamolybdate. 32.88 grams of the product were recovered, representing a yield of 98.03 percent of the theoretical yield.

EXAMPLE 10

Melaminium octamolybdate having a 2/1 molybdenum/melamine molar ratio was prepared by adding 5.00 grams of melamine, 11.42 grams of molybdenum trioxide, 28.57 grams of the sodium salt of benzenesulfonic acid and 300 milliliters of water to a 500 milliliter round-bottom flask equipped with a water-cooled condenser and refluxing the mixture at about 105° C. with continual stirring for 2 hours. The mixture then was cooled to room temperature and was filtered. A white crystalline product was recovered and was washed with water and vacuum dried at 100° C. for 1½ hours. Infrared and x-ray diffraction analyses identified the recovered crystalline product to be melaminium octamolybdate. 15.83 grams of the product were recovered, representing a yield of 94.39 percent of the theoretical yield.

EXAMPLE 11

10.00 grams of melamine, 22.83 grams of molybdenum trioxide, 18.53 grams of sodium chloride and 300 milliliters of water were refluxed with continuous stirring at about 105° C. for two hours in a 500 milliliter round-bottom flask equipped with a water-cooled condenser. The mixture then was cooled to room temperature and filtered. A white crystalline product was recovered. The product was washed with water and vacuum dried at 100° C. for 3 hours. The white product was identified by infrared and x-ray diffraction analyses to be melaminium octamolybdate. 33.34 grams of the white product was recovered, representing a yield of 99.40 percent of the theoretical yield.

EXAMPLE 12

10.00 grams of melamine, 22.83 grams of molybdenum trioxide, 27.64 grams of potassium sulfate and 300 milliliters of water were added to a 500 milliliter round-bottom flask fitted with a water-cooled condenser. The mixture was refluxed at about 105° C. for 2 hours while being continuously stirred and then was cooled to room temperature and filtered. A white crystalline product was recovered. The recovered crystalline product was washed with water and vacuum dried at 100° C. for 3 hours. The product was identified by infrared and x-ray diffraction analyses to be melaminium octamolybdate. 33.61 grams of the product was recovered, representing a yield of 100 percent of the theoretical yield.

EXAMPLE 13

10.00 grams of melamine, 22.83 grams of molybdenum trioxide, 26.96 grams of sodium nitrate and 300 milliliters of water were added to a 500 milliliter round-bottom flask fitted with a water-cooled condenser and were refluxed to about 105° C. for 2 hours while the mixture was being stirred continuously. The mixture then was cooled to room temperature and was filtered. A white crystalline product was recovered. The product was washed with water and vacuum dried at 100° C. for 3 hours. Infrared and x-ray diffraction analyses identified the product to be melaminium octamolybdate. 33.31 grams of the product were recovered, representing a yield of 99.31 percent of the theoretical yield.

EXAMPLE 14

10.00 grams of melamine, 22.83 grams of molybdenum trioxide, 21.86 grams of lithium nitrate and 300 milliliters of water were refluxed for 2 hours at about 105° C. with continuous stirring in a 500 milliliter round-bottom flask equipped with a water-cooled condenser. The mixture was cooled to room temperature and filtered. A white crystalline product was recovered which then was washed with water and vacuum dried at 100° C. for 2½ hours. The product was identified to be melaminium octamolybdate by infrared and x-ray diffraction analyses. 33.28 grams of the product were recovered, representing a yield of 99.22 percent of the theoretical yield.

EXAMPLE 15

10.00 grams of melamine, 22.83 grams of molybdenum trioxide, 39.59 grams of cupric sulfate and 300 milliliters of water were refluxed at about 105° C. with continuous stirring for 2 hours in a 500 milliliter round-bottom flask provided with a water-cooled condenser. At the end of the two-hour period, the mixture was cooled to room temperature and filtered. A white crystalline product that had a slight yellow tint was recovered. The product was washed with water and vacuum dried for 2½ hours at 100° C. Infrared and x-ray diffraction analyses identified the recovered crystalline product to be melaminium octamolybdate. 33.28 grams of product was recovered, representing a yield of 99.22 percent of the theoretical yield.

EXAMPLE 16

The procedure of Example 15 was repeated except that 22.80 grams of zinc sulfate was included in the mixture in place of the 39.59 grams of cupric sulfate. 33.17 grams of a white crystalline product identified by infrared and x-ray diffraction analyses to be melaminium octamolybdate was recovered, representing a yield of 98.90 percent of the theoretical yield.

EXAMPLE 17

The procedure of Example 15 was repeated except that 41.68 grams of nickle sulfate ($NiSO_4.6H_2O$) was included in the mixture in place of the 39.59 grams of cupric sulfate. 33.05 grams of a white crystalline product having a slight green tint identified by infrared and x-ray diffraction analyses to be melaminium octamolybdate was recovered, representing a yield of 98.54 percent of the theoretical yield.

EXAMPLE 18

10.00 grams of melamine, 22.82 grams of molybdenum trioxide, 12.72 grams of ammonium chloride and 300 milliliters of water were charged into a 500 milliliter round-bottom flask fitted with a water-cooled condenser. The mixture was refluxed for 2 hours while continuously being stirred, was cooled to room temperature and then filtered. A white crystalline solid having a slight blue tint was recovered. The solid was washed with water and vacuum dried for 4¼ hours at 120° C. 33.00 grams of the crystalline product, identified by infrared and x-ray diffraction analyses to be melaminium octamolybdate, was recovered representing a yield of 98.39 percent of the theoretical yield.

EXAMPLE 19

10.00 grams of melamine, 22.82 grams of molybdenum trioxide, 24.09 grams of sodium bisulfate and 300 milliliters of water were added to a 500 milliliter round-bottom flask fitted with a water-cooled condenser. The charge was refluxed for 2 hours while being stirred continuously and was cooled to room temperature and filtered. A white crystalline solid having a slight blue tint was recovered. The recovered solid was washed with water and vacuum dried for 4¼ hours at 120° C. Infrared and x-ray diffractin analyses identified the product to be melaminium octamolybdate. 32.41 grams of the crystalline solid was recovered, representing a yield of 96.33 percent of the theoretical yield.

EXAMPLE 20

10.00 grams of melamine, 22.83 grams of molybdenum trioxide, 16.89 grams of sodium sulfate and 300 milliliters of water were added to a 500 milliliter round-bottom flask equipped with a water-cooled condenser. The mixture was refluxed for 2 hours while being stirred continuously. The mixture was cooled to room temperature and filtered. A crystalline solid having a light yellow tint was recovered. The recovered solid was washed with water and was vacuum dried for 1½ hours at 120° C. X-ray diffraction analysis identified the product to be melaminium octamolybdate. 32.82 grams of the product were recovered, representing a yield of 97.85 percent of the theoretical yield.

EXAMPLE 21

10.00 grams of melamine, 22.83 grams of molybdenum trioxide, 8.48 grams of ammonium chloride, 3.17 grams of ammonium nitrate and 300 milliliters of water were added to a 500 milliliter round-bottom flask fitted with a water-cooled condenser. The mixture was refluxed for 2 hours while being stirred continuously and then was cooled to room temperature and filtered. A white crystalline solid was recovered from the liquid phase. The solid was wahsed with water and vacuum dried at 120° C. for 2 hours. X-ray diffraction analysis identified the white product to be melaminium octamolybdate. 32.92 grams of the product were recovered, representing a yield of 98.15 percent of the theoretical yield.

EXAMPLE 22

10.00 grams of melamine, 22.83 grams of molybdenum trioxide, 11.41 grams of ammonium bisulfate and 300 milliliters of water were charged into a 500 milliliter round-bottom flask equipped with a water-cooled condenser. The mixture was refluxed for 2 hours while being stirred continuously, cooled to room temperature and filtered. A white crystalline solid was recovered. The white solid product was washed with water and vacuum dried for 3 hours at 120° C. The product was identified by x-ray diffraction analysis to be melaminium octamolybdate. 33.41 grams of the product were recovered, representing a yield of 99.61 percent of the theoretical yield.

The following Examples 23 through 29 illustrate the use of oxidizing agents in the reaction mixture.

EXAMPLE 23

10.00 grams of melamine, 22.82 grams of molybdenum trioxide, 12.72 grams of ammonium chloride, 0.50 gram of ammonium persulfate and 300 milliliters of water were added to a 500 milliliter round-bottom flask provided with a water-cooled condenser. The mixture was refluxed for 2 hours while being stirred continuously and then was cooled to room temperature and filtered. A white crystalline solid product was separated from the liquid phase. The solid product was washed with water and vacuum dried for 1½ hours at 120° C. Infrared and x-ray diffraction analyses identified the product to be melaminium octamolybdate. 32.28 grams of the product were recovered, representing a yield of 96.24 percent of the theoretical yield.

EXAMPLE 24

10.00 grams of melamine, 22.82 grams of molybdenum trioxide, 24.09 grams of sodium bisulfate, 0.50 gram of ammonium persulfate and 300 milliliters of water were charged into a 500 milliliter round-bottom flask fitted with a water-cooled condenser. The reaction mixture was fluxed for 2 hours while being stirred continuously and, thereafter, was cooled to room m temperature and filtered. A white crystalline product was recovered. The product after being washed with water and vacuum dried for 1½ hours at 120° C. was identified by infrared and x-ray diffraction analyses to be melaminium octamolybdate. 33.09 grams of the product were recovered, representing a yield of 98.66 percent of the theoretical yield.

EXAMPLE 25

10.00 grams of melamine, 22.83 grams of molybdenum trioxide, 10.60 grams of ammonium chloride, 1.18 grams of sodium dichromate and 300 milliliters of water were refluxed in a 500 milliliter round-bottom flask equipped with a water-cooled condenser. The mixture then was cooled to room temperature and filtered. A light yellow crystalline product was recovered. The product was washed with water and vacuum dried for 2 hours at 120° C. The product was identified by x-ray diffraction analysis to be melaminium octamolybdate. 32.51 grams of the product were recovered, representing a yield of 96.93 percent of the theoretical yield. The light yellow color of the crystalline product is attributed to the presence of a small amount of the sodium dichromate in the product (sodium dicromate being bright yellow-orange in color).

EXAMPLE 26

10.00 grams of melamine, 22.83 grams of molybdenum trioxide, 10.60 grams of ammonium chloride, 0.75 gram of potassium pernanganate and 300 milliliters of water were added to a 500 milliliter round-bottom flask provided with a water-cooled condenser. The mixture was refluxed for 2 hours while being stirred continuously, was cooled to room temperature and was filtered. A light peach colored crystalline solid was recovered. The recovered crystalline product was washed with water and vacuum dried for 2 hours at 120° C. X-ray diffraction analysis identified the product to be melaminium octamolybdate. 32.91 grams of the product were recovered, representing a yield of 98.12 percent of the theoretical yield. The light peach color of the crystalline product is believed to result from the presence of a small amount of potassium permanganate in the product.

EXAMPLE 27

10.00 grams of melamine, 22.83 grams of molybdenum trioxide, 10.60 grams of ammonium chloride, 10.00 grams of a 5 percent by weight solution of sodium hypochlorite, and 300 milliliters of water were charged into a 500 milliliter round-bottom flask fitted with a water-cooled condenser. The mixture was refluxed for 2 hours while being stirred continuously and, then, was cooled to room temperature and filtered. A crystalling solid having a pale yellow tint was recovered. The recovered solid was washed with water and vacuum dried for 3 hours at 120° C. The solid product was identified by x-ray diffraction analysis to be melaminium octamolybdate. 33.03 grams of the product were recovered, representing a yield of 98.48 of the theoretical yield.

EXAMPLE 28

10.00 grams of melamine, 22.83 grams of molybdenum trioxide, 10.60 grams of ammonium chloride, 2.00 grams of a 30 percent by weight solution of hydrogen peroxide and 300 milliliters of water were added to a 500 milliliter round-bottom flask provided with a water-cooled condenser. The mixture was refluxed for 2 hours while being stirred continuously. The mixture then was cooled to room temperature and filtered. A crystalline solid having a light yellow color was recovered. The crystalline solid was washed with water and vacuum dried for 1½ hours at 120° C. X-ray diffraction analysis identified the material to be melaminium octamolybdate. 32.76 grams of the product were recovered, representing a yield of 97.67 percent of the theoretical yield.

EXAMPLE 29

10.00 grams of melamine, 22.83 grams of molybdenum trioxide, 12.69 grams of ammonium nitrate and 300 milliliters of water were charged into a 500 milliliter round-bottom flask provided with a water-cooled condenser. The mixture was refluxed for 2 hours while being stirred continuously. The mixture then was cooled to room temperature and filtered. A white crystalline solid was recovered. The recovered solid was washed with water and vacuum dried for 2 hours at 120° C. X-ray diffraction analysis identified the solid to be melaminium octamolybdate. 32.82 grams of the solid were recovered, representing a yield of 97.85 percent of the theoretical yield.

The ammonium nitrate in Example 29 serves a dual function in that it functions as the water-soluble salt additive and as an oxidizing agent.

Although the reaction desirably is carried out at a temperature above 75° C., the reaction may be carried out at temperatures below 75° C., as illustrated by Examples 30 through 35, although a longer reaction time is required as the reaction temperature is lowered. The reaction mixtures used in Examples 30 through 35 consisted of 11.41 grams of molybdenum trioxide 5.00 grams of melamine, 7.86 grams of ammonium sulfate and 150 milliliters of water. The reactions were carried out within the temperature ranges recited in Table I for the periods of time indicated while the mixtures were being continuously stirred. Upon completion of the reaction time, the mixtures were filtered. The solid products recovered were washed with water and vacuum dried at about 100° C. The identification of the solid products recovered was determined by infrared (IR) and x-ray diffraction (XRD) analyses. As illustrated by Examples 30 through 35, higher reaction temperatures and longer reaction times favor the formation of melaminium octamolybdate.

TABLE I

| Ex. | Reaction Temp. (°C.) | Reaction Time (hours) | IR | XRD |
|---|---|---|---|---|
| 30 | 56°–57° | 1 | Kc* | Kc |
| 31 | 43°–46° | 1 | Kc + Ka** | Kc + Ka |
| 32 | 43°–44° | 2 | Kc | Kc |
| 33 | 31°–34° | 2¼ | Kc + Ka | Kc + Ka |
| 34 | RT (25°) | 4 | Kc + Ka | Kc + Ka |
| 35 | RT (25°) | 19½ | Kc | Kc |

*Kc - melaminium octamolybdate
**Ka - melaminium heptamolybdate

Example 30 illustrates that at a reaction temperature ranging from 56°–≡° C. melaminium octamolybdate is formed after only 1 hour reaction time while if the reaction is carried out at the slightly lower temperature range of 42°–46° for 1 hour the reaction is not complete in that the product contains both melaminium octamolybdate and melaminium heptamolybdate. However, if the reaction is extended to 2 hours at even a lower temperature range of 43°–44° C., melaminium octamolybdate is the sole solid product recovered (see Example 32). When the reaction temperature range is lowered to 31°–34° C., the formation of melaminium octamolybdate is not complete after a reaction time of 2¼ hours (see Example 33). At room temperature, the formation of melaminium octamolybdate as the sole solid product is not complete with a reaction time of 4 hours (see Example 34), but is complete after a reaction time of 19½ hours (see Example 35).

The following Examples 36 through 38 illustrate the recycling of the liquid phase in the process with the addition only of melamine and molybdenum trioxide.

EXAMPLE 36

10.00 grams of melamine, 22.83 grams of molybdenum trioxide, 15.72 grams of ammonium sulfate and 300 milliliters of water were charged into a 500 milliliter round-bottom flask equipped with a water-cooled condenser. The reaction mixture was heated to about 100° C. and was refluxed for 2 hours while being stirred continuously. The reaction mixture was cooled to room temperature and was filtered. A while crystalline product was recovered. The recovered product was washed with water and vacuum dried for 2 hours at 100° C. Infrared analysis identified the product to be melaminium octamolybdate. 33.23 grams of the crystalline product was recovered, representing a yield of 99.08 percent of the theoretical yield.

EXAMPLE 37

10.00 grams of melamine and 22.83 grams of molybdenum trioxide were added to the 295 milliliters of filtrate recovered from Example 25 and the resulting mixture while being stirred continuously was refluxed at about 100° C. for 2 hours in a 500 milliliter round-bottom flask provided with a water-cooled condenser. The mixture then was cooled to room temperature and filtered. A white crystalline product was recovered and was washed with water and vacuum dried at 100° C. for 2 hours. The product was identified by infrared analysis to be melaminium octamolybdate. 33.06 grams of the product was recovered, representing a yield of 98.57 percent of the theoretical yield.

EXAMPLE 38

10.00 grams of melamine and 22.83 grams of molybdenum trioxide were added to the 290 milliliters of filtrate recovered from Example 26. The mixture while being stirred continuously was refluxed at about 100° C. for 2 hours in a 500 milliliter round-bottom flask provided with a water-cooled condenser. The mixture then was cooled to about room temperature and was filtered. A white crystalline solid was recovered. The recovered product was washed with water and vacuum dried at 100° C. for 2 hours. Infrared analysis identified the product to be melaminium octamolybdate. 33.17 grams of the white crystalline product was recovered, representing a yield of 98.90 percent of the theoretical yield.

The following Examples 39 and 40 illustrate reactions between molybdenum trioxide and melamine in mixtures which contain no water-soluble salt additive.

EXAMPLE 39

10.00 grams of melamine, 22.83 grams of molybdenum trioxide and 300 milliliters of water were added to a 500 milliliter round-bottom flask provided with a water-cooled condenser. The mixture was refluxed for 4 hours while being stirred continuously. The mixture then was cooled to room temperature. A thick slurry resulted. The slurry was filtered and the recovered solid was washed with water and vacuum dried at 100° C. for 16 hours. A product having a blue tint was recovered. X-ray diffraction analysis indicated that the product was made up in part of melaminium octamolybdate and contained one or more unknown components.

Contrasting the reaction of Example 39 with the results of the reactions of Examples 6, 9-16, 19 and 21-24, it becomes apparent that the presence of the water-soluble salt additive results in the reaction being completed in a shorter time (than when the water-soluble salt is omitted from the reaction) and that a product of higher quality results when the water-soluble salt is present.

EXAMPLE 40

A reaction mixture of the same composition as used in Example 39 was refluxed in a 500 milliliter round-bottom flask provided with a water-cooled condenser for approximately 16 hours while being stirred continuously. The mixture then was cooled to room temperature. A thick "jellied" slurry was obtained. The slurry was filtered and the recovered solid was washed with water and vacuum dried at 116° C. for 2 1/6 hours. A product having a blue tint was recovered. X-ray diffraction analysis indicated that the product contained in part melaminium octamolybdate and comprised at least one other unidentified component.

Example 40 illustrates that even after about 16 hours reaction time, the reaction was not complete when the water-soluble salt is absent from the reaction mixture.

The amine molybdates produced by the process of this invention are useful as smoke retardant additives for vinyl chloride polymer and vinylidene chloride polymer compositions.

The process of this invention may produce a liquid amine molybdate, depending upon the materials used, instead of a solid product.

I claim:

1. A process for making an amine molybdate comprising reacting essentially stoichiometric quantities of molybdenum trioxide with an amine in an aqueous medium essentially free of acid and in which is dissolved a water-soluble ammonium or monovalent metal or divalent metal or trivalent rare earth metal salt of an acid or a combination of one or more of said water-soluble salts.

2. The process of claim 1 wherein the said water-soluble salt is present in an amount sufficient at least to equal a 1:1 mole ratio with the molybdenum trioxide.

3. The process of claim 1 wherein the reaction mixture contains an oxidizing agent.

4. The process of claim 3 wherein the said oxidizing agent is present in an amount up to 10 percent by weight of the molybdenum trioxide present in the reaction mixture.

5. The process of claim 1 wherein the reaction mixture is refluxed for from $\frac{1}{4}$ to 4 hours and the solid component of the reaction mixture thereafter is separated from the liquid component of the reacted mixture.

6. The process of claim 5 wherein the said liquid component separated from the reacted mixture is used as the liquid phase to which essentially stoichiometric quantities of molybdenum trioxide and an amine are added to produce a reaction mixture for repeating the said process.

7. The process of claims 1, 2 or 3 wherein the said amine molybdate is melamine and is present in an amount to form a 2 to 1 molybdenum to melamine molar ratio.

8. The process of claims 1, 2, 3, 4, 5 or 6 wherein the reaction mixture is heated to between about 75° to 110° C.

9. The process of claim 5 wherein the said reacted mixture is cooled to about room temperature before the said separation of the solid component of the reacted mixture from the liquid component of the reacted mixture.

10. The process of claim 7 wherein the reaction mixture is heated to between about 75° to 110° C.

11. The process of claims 1, 2, 3, 4, 5 or 6 wherein the said reaction between the molybdenum trioxide and amine occurs at a temperature between about 25° 1 to 110° C.

12. The process of claim 7 wherein the said reaction between the molybdenum trioxide and amine occurs at a temperature between about 25° to 110° 1 C.

* * * * *